United States Patent
Deshmukh et al.

(10) Patent No.: US 8,698,098 B2
(45) Date of Patent: Apr. 15, 2014

(54) IN SITU HOLDER ASSEMBLY

(75) Inventors: Pushkarraj V. Deshmukh, Pittsburgh, PA (US); Jeffrey J. Gronsky, Ligonier, PA (US); Paul E. Fischione, Export, PA (US)

(73) Assignee: E.A. Fischione Instruments, Inc., Export, PA (US)

( * ) Notice: Subject to any disclaimer, the term of this patent is extended or adjusted under 35 U.S.C. 154(b) by 4 days.

(21) Appl. No.: 13/466,947

(22) Filed: May 8, 2012

(65) Prior Publication Data

US 2013/0119267 A1 May 16, 2013

Related U.S. Application Data

(63) Continuation-in-part of application No. 12/847,167, filed on Jul. 30, 2010, now Pat. No. 8,178,851.

(51) Int. Cl.
*G01N 21/01* (2006.01)
*G01N 23/00* (2006.01)

(52) U.S. Cl.
USPC ............. 250/440.11; 250/442.11; 250/491.1; 378/208; 73/864.91

(58) Field of Classification Search
USPC .......... 250/440.11, 442.11, 491.1; 73/864.91; 378/208
See application file for complete search history.

(56) References Cited

U.S. PATENT DOCUMENTS

| | | | |
|---|---|---|---|
| 4,229,640 A | 10/1980 | Castellani Longo | |
| 4,591,722 A | 5/1986 | Biddlecombe et al. | |
| 5,326,971 A | 7/1994 | Theodore et al. | |
| 6,080,956 A | 6/2000 | Ueda et al. | |
| 8,178,851 B2 * | 5/2012 | Deshmukh et al. | 250/440.11 |
| 8,189,737 B2 * | 5/2012 | Keller et al. | 378/18 |
| 8,336,405 B2 * | 12/2012 | Stabacinskiene et al. | 73/864.91 |
| 2005/0186776 A1 | 8/2005 | Borden et al. | |
| 2005/0279938 A1 | 12/2005 | Moses et al. | |
| 2006/0044554 A1 | 3/2006 | Mertz et al. | |
| 2008/0015557 A1 | 1/2008 | Chan et al. | |
| 2008/0283748 A1 | 11/2008 | Matsumoto et al. | |

FOREIGN PATENT DOCUMENTS

JP 08031361 2/1996

OTHER PUBLICATIONS

High-speed transmission electron microscope, H. Domer and O. Bostanjoglo, Rev. Sci. Instrum., 74 (10), 4369-4372 (2003).

(Continued)

*Primary Examiner* — Nikita Wells
(74) *Attorney, Agent, or Firm* — Neal P. Pierotti; Metz Lewis Brodman Must O'Keefe LLC

(57) ABSTRACT

An in situ optical specimen holder is disclosed which allows imaging and analysis during dynamic experimentation. This holder assembly includes a set of focusing and reflection optics along with an environmental cell. Electromagnetic radiation can be used to optically excite the specimen in the presence or absence of fluid and the source of such radiation may be located within the body of the holder itself. The spot size of the irradiation at the specimen surface can be varied, thus exciting only a specific region on the specimen. The window type cell provides a variable fluid path length ranging from the specimen thickness to 500 μm. The holder has the provision to continuously circulate fluids over the specimen. The pressure within the cell can be regulated by controlling the flow rate of the fluids and the speed of the pumps.

41 Claims, 14 Drawing Sheets

(56) References Cited

OTHER PUBLICATIONS

Development of a multifunctional TEM specimen holder equipped with a piezodriving probe and a laser irradiation port, D. Shindo et al., J. Electron Microsc., vol. 58, No. 4, 245-249 (2009).

Single-shot dynamic transmission electron microscopy, T. LaGrange et al., Appl. Phys. Lett., 89, 044105 (2006).

Four-dimensional ultrafast electron microscopy, V. Lobastov et al., PNAS, vol. 102, No. 20 (2005).

Local Heating of Specimen with Laser Diode in TEM, A. Takaoka et al., J. Electron Microsc., vol. 38, No. 2, 95-100 (1989).

Kinetics of Laser-Induced Crystallization of Amorphous Germanium Films, O. Bostanjoglo and E. Endruschat, Phys. Stat. Sol. (a) 91, 17 (1985).

\* cited by examiner

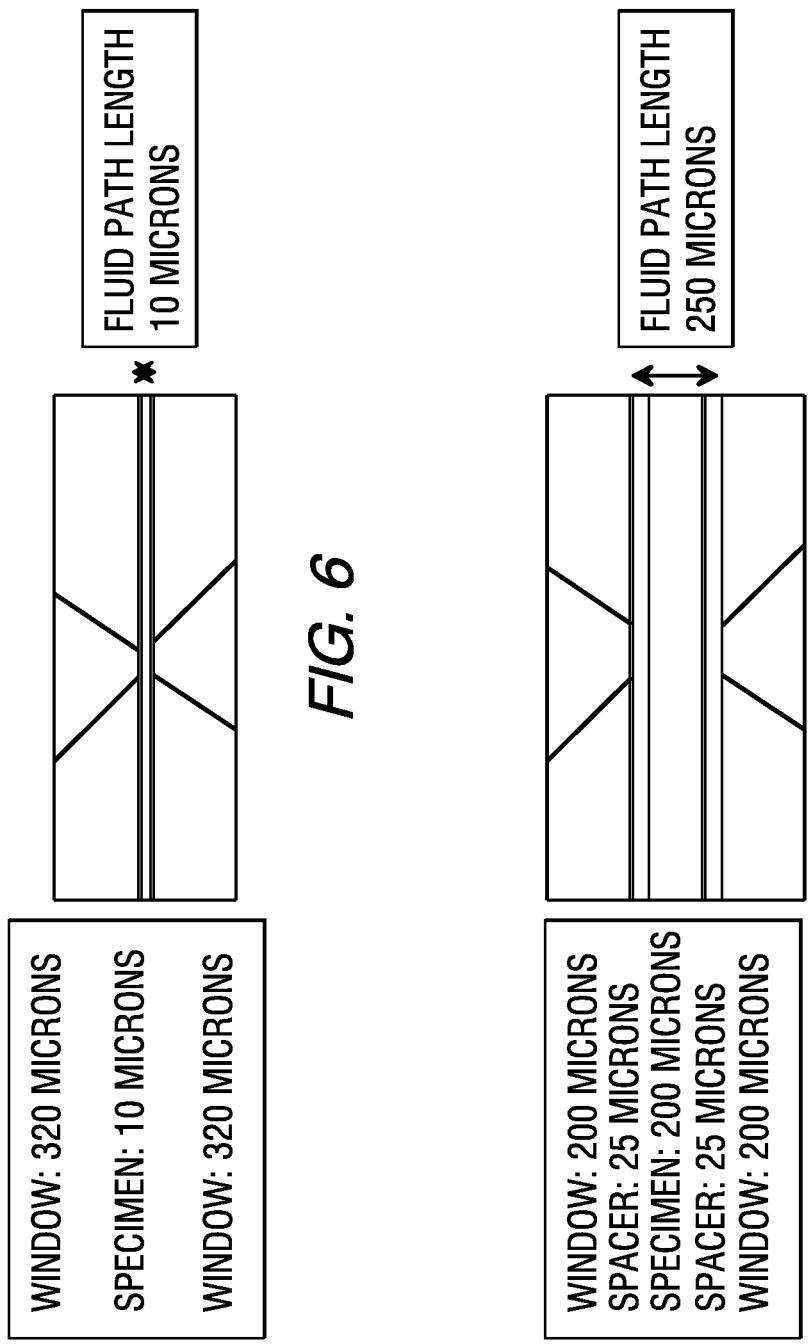

IN SITU HOLDER ASSEMBLY

CROSS REFERENCE TO RELATED APPLICATIONS

This application claims the benefit of co-pending U.S. application Ser. No. 12/847,167, filed Jul. 30, 2010.

BACKGROUND OF THE INVENTION

1. Field of the Invention

The invention relates to specimen holders that allow imaging and analysis and particularly to in situ holders capable of exciting a specimen for dynamic experimentation.

2. Description of the Prior Art

In situ is a Latin phrase meaning "in the place." The ability to observe dynamic processes directly, close to their natural state as they undergo changes is vital for the advancement of research in many modern day applications. Various examples of in situ holders for transmission electron microscopy (TEM) include cooling holders, heating holders, nano indentation holders, straining holders, biasing holders and environmental cell holders. Holders are also utilized in a variety of other imaging and analysis devices.

Observations that require the presence of controlled environmental fluids around the specimen at elevated temperatures is one challenging aspect of in situ imaging and analysis. Fluids referred herein may include liquids, gases or plasma. An electron beam, such as that utilized by a TEM to create a specimen image, interacts strongly with matter. This leads to electron beam broadening which is detrimental to image resolution. To avoid extraneous scattering of the electron beam, it is desirable to have a very low-pressure beam path within the TEM column, optimally a high vacuum environment. A specimen immersed in fluids, opposes this basic principle. This limits the in situ environment height adjacent the specimen to less than a few hundred microns, making it extremely difficult to incorporate a heating system within the confined space of the holder necessary to create such an environment. Apart from this, high temperatures also give rise to specimen drift because of asymmetrical thermal expansion of the holder and consequential displacement of the specimen within the TEM. The presence of these fluids, therefore, decreases the resolution of the microscope images, limiting the amount of useful information that can be gathered.

In situ experimentation that requires the presence of fluids is carried out with the help of an environmental cell (E-Cell) that is part of the specimen holder. Typically, such a cell consists of two thin film windows, which completely seal a confined space around the specimen to provide a controlled atmosphere for in situ experimentation. The basic requirement for such a device is to contain the fluid within the cell so that the main microscope vacuum remains undisturbed.

Traditionally, heating holders employed resistive heating to elevate the specimen temperature. FIG. 1a and 1b illustrate the basic principle of resistive heater 100 utilized within a TEM specimen holder. Here, an electrical current is passed through a resistance coil 102, which is either wrapped around, as in FIG. 1a, or placed near the specimen cup 104, as in FIG. 1b, containing a TEM specimen 106 as shown. This generates heat within the coil, which in turn heats the specimen either by conduction, as in FIG. 1a or by radiation, as in FIG. 1b. This heating technology is highly constrained when used for in situ heating of a specimen within an environmental cell that contains fluids. The major limitations of these prior art systems include several factors. First, resistive heating requires a complex heating mechanism, which comprises many parts, including resistance coils, radiation shields, electrical connectors and insulating blocks. This complete assembly occupies a large volume. This technology, when incorporated within an in situ holder, would increase the fluid path length of the cell and dramatically reduce the image resolution of the specimen. Resistive heaters, furthermore, have a limited working life. The heating coils may last only a few hours, especially in the presence of gaseous oxidizing, reactive or reducing environments. Conduction and radiation from the heating coils not only heat the specimen but also the entire surrounding region of the environmental cell as well as the microscope goniometer or adjacent parts of other imaging or analytical devices. This introduces significant specimen drift, thereby limiting image resolution. It is also not possible to use resistive heating coils for the localized heating of the specimen.

Resistive heating is also limited by the maximum specimen temperature that can be achieved, generally limited to the range of 1,000° C. to 1,200° C. Moreover, the use of electrical current for heating can generate an electromagnetic field around the specimen, which may interfere with the electron imaging beam, limiting the image resolution and causing beam drift. Lastly, in light of the inefficient heating mechanism, the time required to attain steady state specimen temperatures can be significant. Most dynamic processes occur within a fraction of a second. This makes the use of resistive heating technology difficult for most modern imaging applications.

Some current TEM holders employ microelectromechanical systems (MEMS) which allow the imaging of the specimen at elevated temperatures as illustrated in FIGS. 2a and 2b. A MEMS-based system 120 utilizes two facing dies made from a silicon substrate; bottom die 122 and top die 124, with a central hole 126. Membranes 128, typically constructed of silicon nitride cover the central hole 126 of each die. These membranes form a gas-flow channel 129 with an inlet 130 and an outlet 132. This nanoreactor membrane contains an embedded heater 134 in the form of a thin platinum wire 136, as shown in FIG. 2b. The heating capability of up to 500° C. is derived from local electrical resistive heating of the platinum wire 136. The compact design of the MEMS based system provides a fluid path length of less than 10 microns and a stable and rapid specimen heating environment of less than one second.

There are, however, many shortcomings associated with such devices. The MEMS based TEM holders are designed to allow the imaging of small specimens such as particles. These holders cannot be used to observe a standard TEM specimen having a diameter of 3 mm. The specimen viewing area in a MEMS based holder is limited to a few square microns. In the MEMS based system the particle specimen is in contact with the silicon nitride membrane. This limits its use to a specimen temperature of less than 1,500° C. Lastly, the reaction chamber in a MEMS based holder is often limited to one time use.

One approach devised to carry out in situ gas flow experiments is the use of an environmental transmission electron microscope (ETEM). This is a term coined for TEM's modified to include a differentially pumped E-Cell. This ETEM consists of radial holes incorporated in the objective lens pole pieces for the first stage of differential pumping. The regular sample area of the ETEM is the controlled environment volume. Differential pumping systems are connected between apertures using appropriate vacuum pump technology. This permits higher gas pressure in the sample region, while maintaining high vacuum conditions in the remainder of the TEM column. A conventional reactor-type gas manifold system enables inlet of flowing gases into the ETEM, and a sample stage with a furnace allows samples to be heated.

The use of ETEM for in situ experiments has many disadvantages: (i) the high installation and operating cost of ETEM, especially to carry out only a dedicated set of experiments; (ii) ETEM can be used only to circulate gases over the specimen; (iii) since the ETEM does not have a completely sealed E-Cell, the gas pressure around the specimen may fail to replicate real life conditions, as it is necessary to observe gas-solid reactions at a specific atmospheric pressure; (iv) the gas path length within the ETEM is considerably large; (v) the gas circulation within the ETEM may contaminate the region around the objective lens pole pieces, which, apart from affecting the image resolution, could also affect the results of the next specimen analysis, which may require a different gaseous environment; (vi) it does not include a specimen heating system and heating has to be carried out using a standard heating specimen holder; and (vii) the partial pressure of any residual gas contained in the microscope column may negatively impact the experimental results.

Laser-induced breakdown spectroscopy (LIBS) is a type of atomic emission spectroscopy which utilizes a highly energetic laser pulse as the excitation source. LIBS operates by focusing the laser onto a small area at the surface of the specimen; when the laser is discharged it ablates a very small amount of material, in the range of picograms to nanograms, which instantaneously generates a plasma plume with temperatures of about 10,000-20,000 K. At these temperatures, the ablated material dissociates into excited ionic and atomic species. During this time, the plasma emits a continuum of radiation which does not contain any useful information about the species present, but within a very small timeframe the plasma expands at supersonic velocities and cools. At this point the characteristic atomic emission lines of the elements can be observed. O. Bostanjoglo and E. Endruschat, in "Kinetics of Laser-induced Crystallization of Amorphous Germanium Films", Phys. Stat. Sol. (a), 91, 17 (1985), and H. Domer and O. Bostanjoglo, in "High-speed transmission electron microscope", Rev. Sci. Instrum., 74 (10), 4369-4372, (2003) disclose a Q-switched Nd-YAG laser system attached to a TEM to investigate the crystallization of amorphous Ge films by time resolved microscopy. A. Takaoka, N. Nakamura, K. Ura, H. Nishi, and T. Hata disclose, in "Local Heating of Specimen with Laser Diode in TEM", J. Electron Microsc., Vol. 38, No. 2, 95-100, 1989, heating specimens locally to a temperature greater than 1,000° C. by introducing a laser diode and small lens system into the vacuum space in the TEM. Some prominent laboratories have modified commercial TEM's by setting up an elaborate network of laser optics in order to pulse the electron beam as well as ablate the specimen. V. A. Lobastov, R. Srinivasan, and A. H. Zewail disclose, in "Four-dimensional ultrafast electron microscopy", PNAS, Vol. 102, No. 20, 2005, a diode-pumped modelocked Ti:Sapphire laser oscillator to develop a 4D ultra fast electron microscope. Here the laser is used to generate ultra fast electron pulses derived from a train of femtosecond pulses and concurrently heat the specimen and induce melting of metals. Similarly, T. LaGrange et. al., disclose, in "Single-shot dynamic transmission electron microscopy", Appl. Phys. Lett., 89, 044105, 2006, the modification of a commercial JEOL2000 TEM and designed a dynamic transmission electron microscope (DTEM) with the help of an Nd-YAG laser system. This DTEM is used for vast arrays of applications including the in situ analysis of Nano wire catalysis and growth.

D. Shindo et. al., in "Development of a multifunctional TEM specimen holder equipped with a piezodriving probe and a laser irradiation port", J. Electron Microsc., Vol. 58, No. 4, 245-249, 2009, disclose the development of a specimen holder to introduce laser irradiation onto the specimen to study various photo-induced phenomena. While this holder has the capability of introducing a laser beam onto the specimen, it does not have: (i) a provision for an E-Cell to observe the dynamic reactions between specimen and fluids; (ii) the ability to focus or adjust the laser beam and, most importantly, (iii) the ability to change the energy level, especially in the form of heat, of the specimen.

Many of these references highlight the importance of lasers in the field of imaging and analysis. They describe various forms of TEM's that have been modified to focus a laser beam onto the specimen. They do not, however, have any provision for a self contained specimen holder which permits the adjustment of the beam and the selective flow of fluids over the specimen in a controlled environment. Many of the references introduce the laser or other light source solely for the observation of the effect of the light source on the specimen. Moreover, the custom installation and operating cost of such modified TEMs are usually very high and the modifications are made to carry out very specific sets of experiments.

There remains a need, therefore, for an optimized in situ holder for the dynamic observation at elevated temperatures in the presence or absence of fluids. Such an in situ holder should have the capability of introducing a beam of electromagnetic radiation through the specimen holder and should be compatible with most major commercially available TEM's. It should be portable and should not involve any modification to the microscope for in situ microscopy.

The holder should accept a wide range of specimens, including a 3 mm diameter disk, particles dispersed on a grid or FIB lamellae contained on a support grid, and further should incorporate a compact heating design in order to minimize the fluid path length within the environmental cell. It should further provide the ability to heat the specimen in the presence of fluids to a temperature in excess of 2,000° C., while also providing the capability to heat a localized region of the specimen. This capability will also limit the amount of heat radiated and conducted from the hot specimen to the surrounding region of the environmental cell and microscope components, reducing specimen drift and minimizing the amount of energy required to reach the desired specimen temperature. Finally, it should provide the capability for thermal cycling of the specimen with a short time interval, while incorporating high steady state specimen temperatures in a small time duration.

SUMMARY OF THE INVENTION

A specimen holder is disclosed having the benefits of previously known in situ heating and environmental cell holders, while allowing for high temperature localized heating of the specimen in the presence or absence of fluids, using electromagnetic radiation. The holder includes an optical assembly to focus electromagnetic radiation onto the specimen to optically excite the specimen in a well defined and limited area. The optical components of this holder can also be adapted for applications such as cathodoluminescence detection, x-ray fluorescence and photoluminescence.

For heating applications, a source of electromagnetic radiation, such as a laser having a fixed wavelength, is attached to the holder. This may be accomplished using a standard connector for an external laser, or the laser diode may be incorporated into the holder housing itself. In the external embodiment, the laser beam enters the holder through a collimator that helps maintain a parallel laser beam path as it travels along the length of the holder barrel. A converging lens module may be assembled proximate to the collimator or alternatively, near the specimen end of the holder barrel. The spot diameter of the laser beam, which preferably ranges from 10-60 microns, on the specimen can be varied by translating this converging lens module to locally heat the specimen in a limited manner. It should be noted in certain applications, particularly in the life sciences, a broader beam may be utilized having a spot size of 100-500 microns. In the internal embodiment, a laser diode is mounted internally to the housing and may be associated with a collimator lens proximate to the diode. The laser power is preferably 0.1-10 watts with a wavelength range of 1-1.1 microns. A battery powered laser may also be utilized, permitting an entirely self-contained radiation source in the holder. These embodiments improve the portability of the holder as a unit. It should also be specifically noted that the internally mounted laser is particularly adapted to operating conditions conducive to utilization of a commercially available laser diode. Use of such a commercial diode, which may be purchased in an off-the-shelf manner, makes the holder more economical. Most importantly, however, it provides the user with the ability to quickly and easily interchange the laser source based upon application conditions or experimental or research requirements. Both the optical and laser components may be interchanged by the user to vary the operation of the device. In either embodiment, the device is designed to minimize thermally induced drift and mechanical displacement of the holder itself, as well as the holder as mounted within the TEM. The laser may further incorporate low power level sources which minimize such thermally induced drift.

The converged laser beam is further reflected onto the specimen with the help of a mirror or a polished surface on the holder tip. The angular position of the mirror is such that the laser beam nominally strikes the center of the specimen. The dimension and position of the minor can also be varied based on the application to obtain the desired irradiation effect on the specimen. A few examples of such mirrors include convex, concave and spherical minors.

When laser irradiation is used, as in the preferred embodiment, a radial, symmetric heating zone is generated on the specimen. This allows for uniform expansion of the specimen at high temperatures, minimizing specimen drift from uneven thermal expansion or contraction across the specimen. The maximum temperature that can be attained by the specimen is limited largely by the material properties of the specimen and the laser power, thus creating a potential for applications in an extraordinary range of fields including catalysis, chemical vapor deposition, and molecular beam epitaxy.

At any given time, imaging and analysis is carried out on a small specimen region. Thus, it is not required to heat the entire specimen. Spot heating of the specimen also reduces the energy and the time required to achieve a given steady state specimen temperature. Heat radiated from the specimen increases exponentially with the increase in the heated surface area. Hence, spot heating of the specimen reduces the heat radiation exponentially. This keeps the surrounding region of the holder close to ambient temperatures and reduces drift, which in turn enhances resolution. Localized heating of the specimen also reduces the heat conduction to other parts of the holder therefore minimizing thermal drift of the device as a whole.

The electromagnetic radiation may be modulated using a computer program. This provides dynamic thermal cycling of the specimen between ambient and elevated temperatures. Further, a pulsed laser can be attached to the holder to provide pulses of energy as small as a few nanoseconds for specific applications.

Unlike a MEMS heating holder, this holder can be used with standard TEM specimen types, as well as non-traditional specimens such as cones, pillars and lamellae.

The environmental cell on the specimen holder provides a controlled atmosphere for in situ observations and analsyis. This cell preferentially consists of a pair of thin windows separated by spacers. The specimen is placed between the thermally insulating spacers. A particular O-ring sealing mechanism provides the user with the flexibility to choose the desired fluid path length. Since there is no heating element present within the E-Cell, the holder can be used with a fluid path length as small as the specimen thickness. An optimum fluid path length can be selected based on the required specimen temperature and the acceptable image resolution. The inlet and outlet conduits allow the entrance and the exit of fluids from the environmental cell.

The holder, together with its particular features and advantages, will become more apparent from the following detailed description and with reference to the appended drawings.

DESCRIPTION OF THE DRAWINGS

FIG. 4b is a sectional isometric view of the second embodiment of the handle portion illustrated in FIG. 4a.

FIG. 6 is a diagrammatic representation of a small fluid path length within the E-cell.

FIG. 7 is a diagrammatic representation of a second fluid path length within the E-cell.

FIG. 10b is a sectional view of the third embodiment of the handle portion illustrated in FIG. 10a.

DESCRIPTION OF THE PREFERRED EMBODIMENTS

Figure 10:
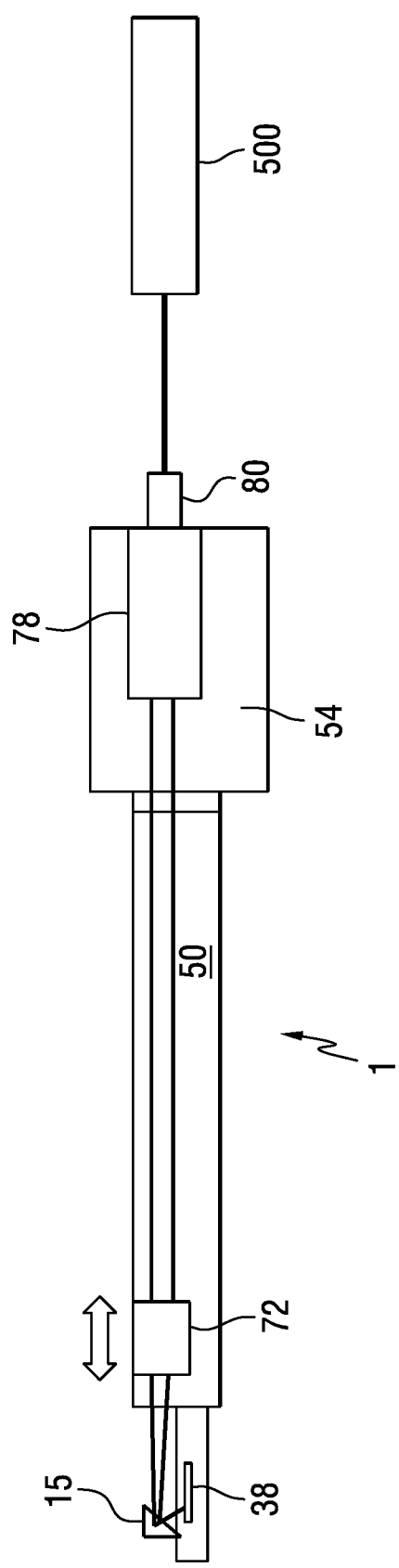
FIG. 10 is a schematic view of the complete in situ holder describing the complete optical assembly of the present invention.

The present invention will be described in detail with respect to its preferred embodiment which is a specimen holder for a transmission electron microscope. FIG. 4 shows an isometric view of the complete in situ holder assembly 1. Assembly 1 is of a conventional design, which, as known to those skilled in the art, may take a variety of forms to accommodate various microscopes produced by various manufacturers. The mechanical needs of each device result in varying geometries of barrel 50 with respect to length, diameter and location of components. Generally, assembly 1 is comprised a holder tip 2 which contains the E-Cell 4 and the primary operative components of the assembly. Holder tip 2 is supported and restrained at the appropriate location within the microscope by barrel 50, which may be designed with a variety of diameters and lengths. At least one O-ring 48, or other seal known to one skilled in the art, is disposed along the length of barrel 50 to seal the internal environment of the microscope from ambient air. A laser assembly 500 or laser 500', or other electromagnetic radiation source (as shown in FIGS. 10; 4a-4b, respectively) is disposed near the non-operative end of barrel 50 and is positioned to be located outside of the microscope environment when in use. As shown in FIG. 4, a standard laser connector 80 and fluid connectors 82 are provided to supply laser irradiation and the in situ environment, in accordance with common practice of those skilled in the art. FIGS. 4a and 4b illustrate a second embodiment which incorporates a laser diode 500' within the handle 54 which is connected to a power source through connection 502. An alternative, adjustable collimating lens 78' may be provided in any embodiment to collimate the laser radiation for transmission to the environmental cell, as will be described more fully with reference to FIGS. 10-10b. Fluid communicates through fluid connectors 82 to fluid conduits 22a and 22b, as will be more fully explained with reference to FIGS. 3 and 5. Additionally, it is to be specifically noted that a battery or other portable and potentially rechargeable power source may be contained within handle 54 and electronically connected to the laser 500'. It would be well within the knowledge of one skilled in the art to locate and interconnect the laser 500' and such power source. It is to be specifically noted that the laser may be substituted with any appropriate electromagnetic radiation beam generator, including X-rays and visible light. Laser 500' is mounted within laser housing 84, which is easily removable from handle 54 and engaged thereto. This facilitates the interchange of radiation sources, as well as maintenance of the source.

Figure 1A:
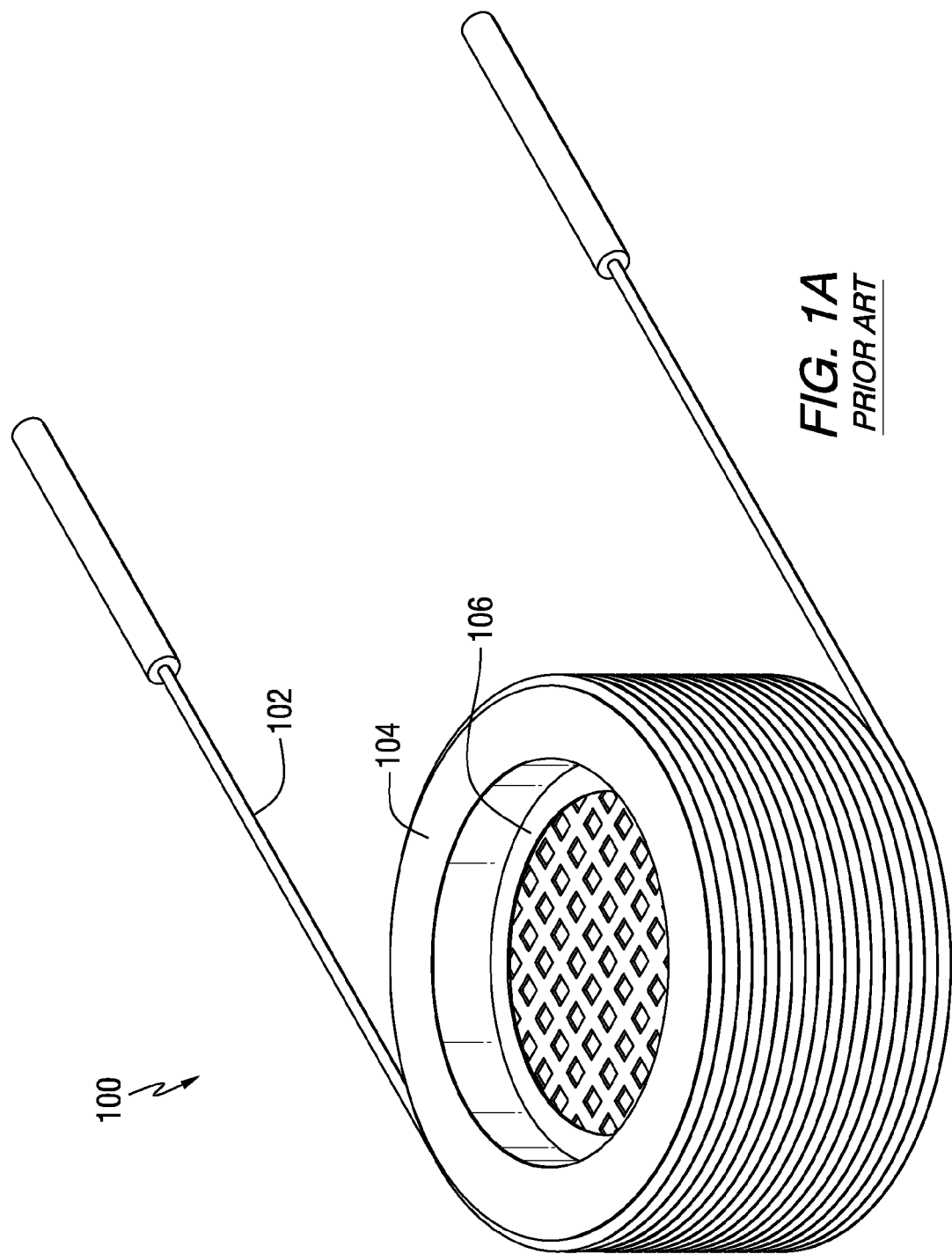
FIG. 1a and 1b are diagrammatic representations of prior art TEM resistance heating devices.
Figure 1B:
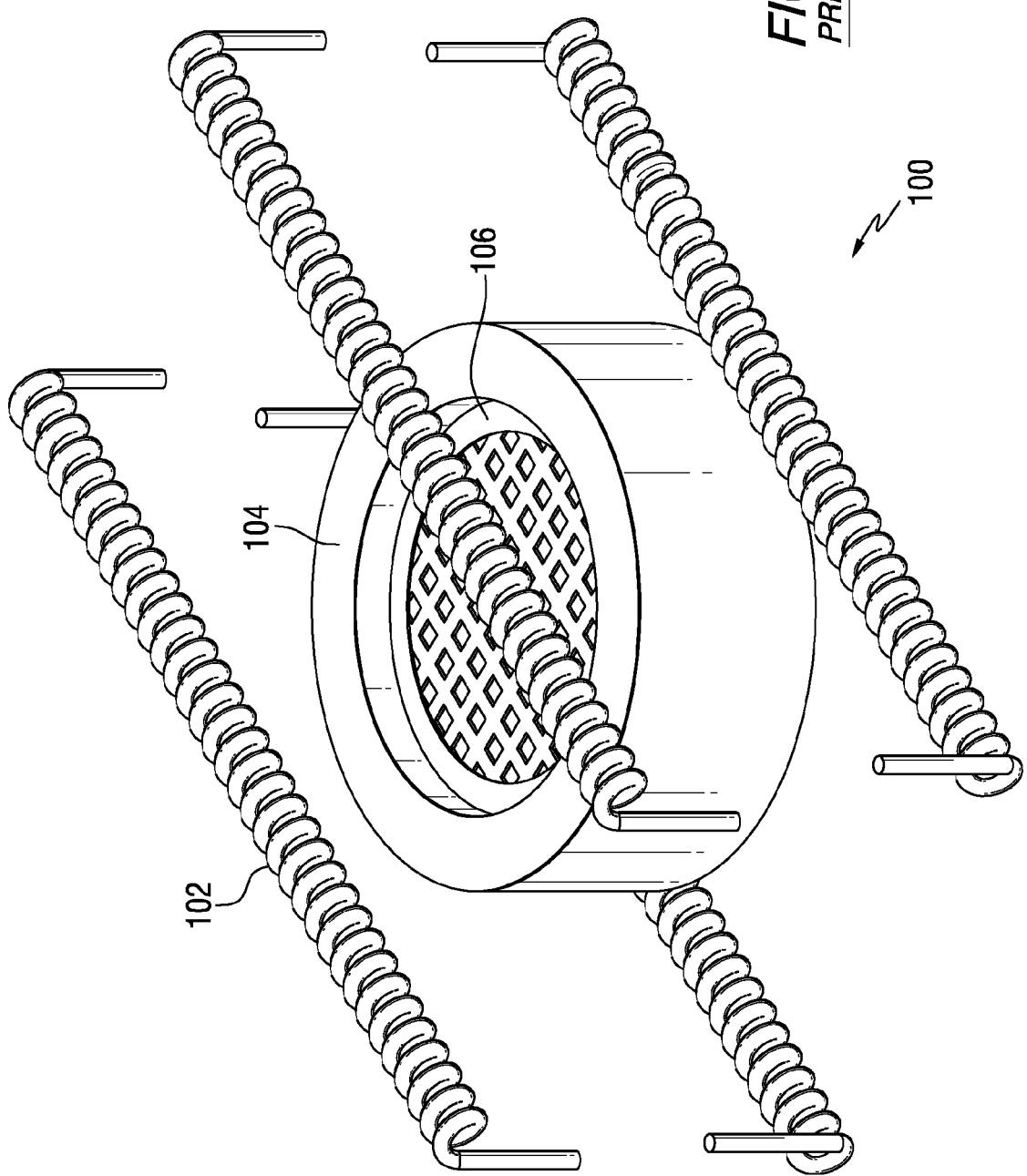
Figure 2A:
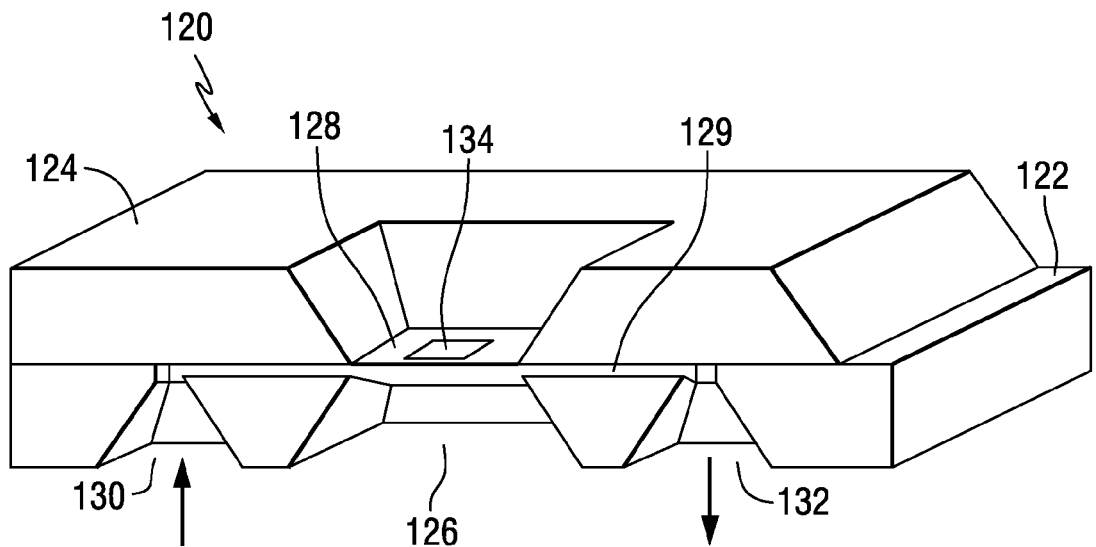
FIGS. 2a and 2b are diagrammatic representations illustrating selective components of a prior art MEMS heating device.
Figure 2B:
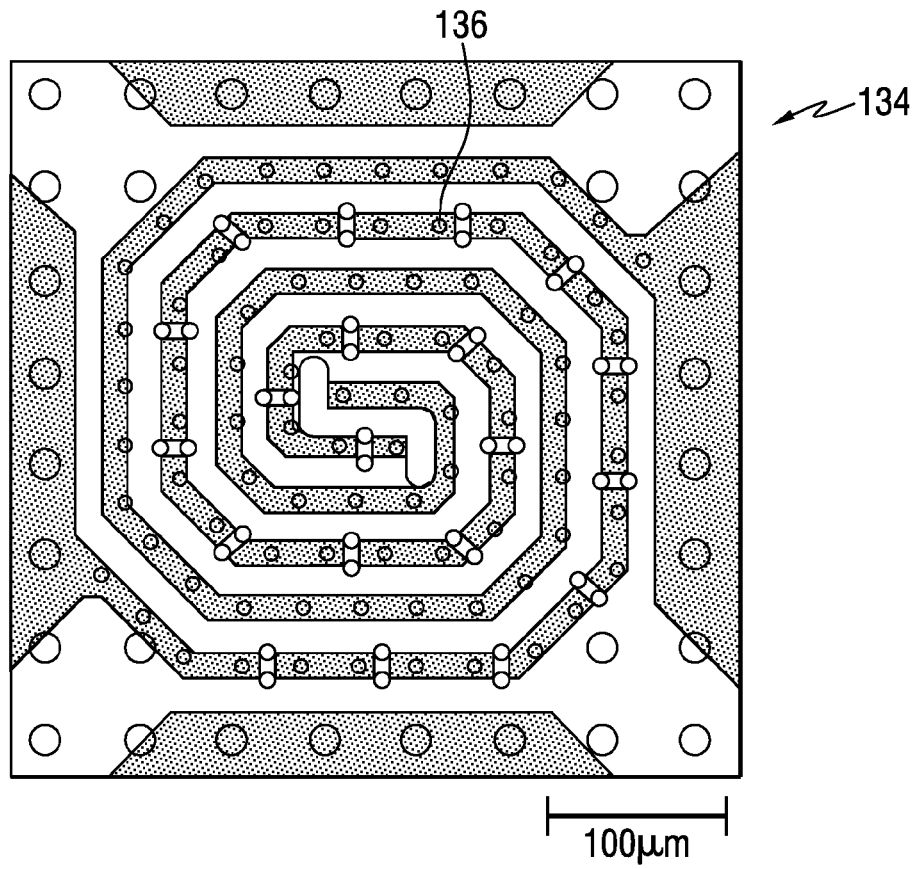
Figure 3A:
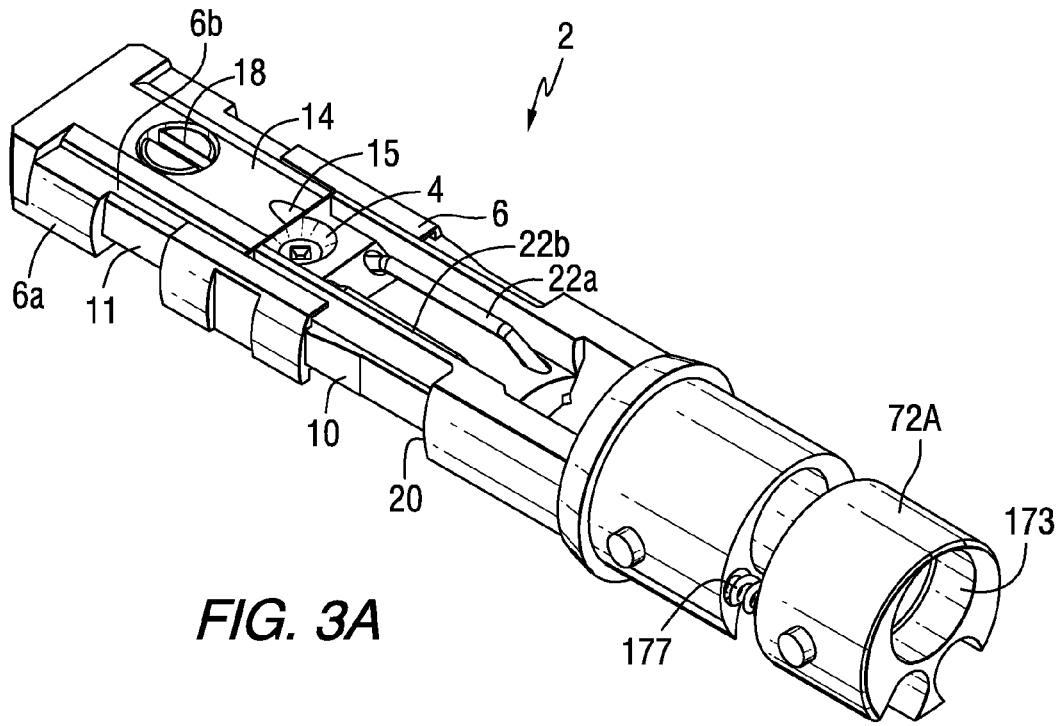
FIG. 3a is a top isometric view of the in situ holder tip assembly in accordance with an embodiment of the present invention.
Figure 3B:
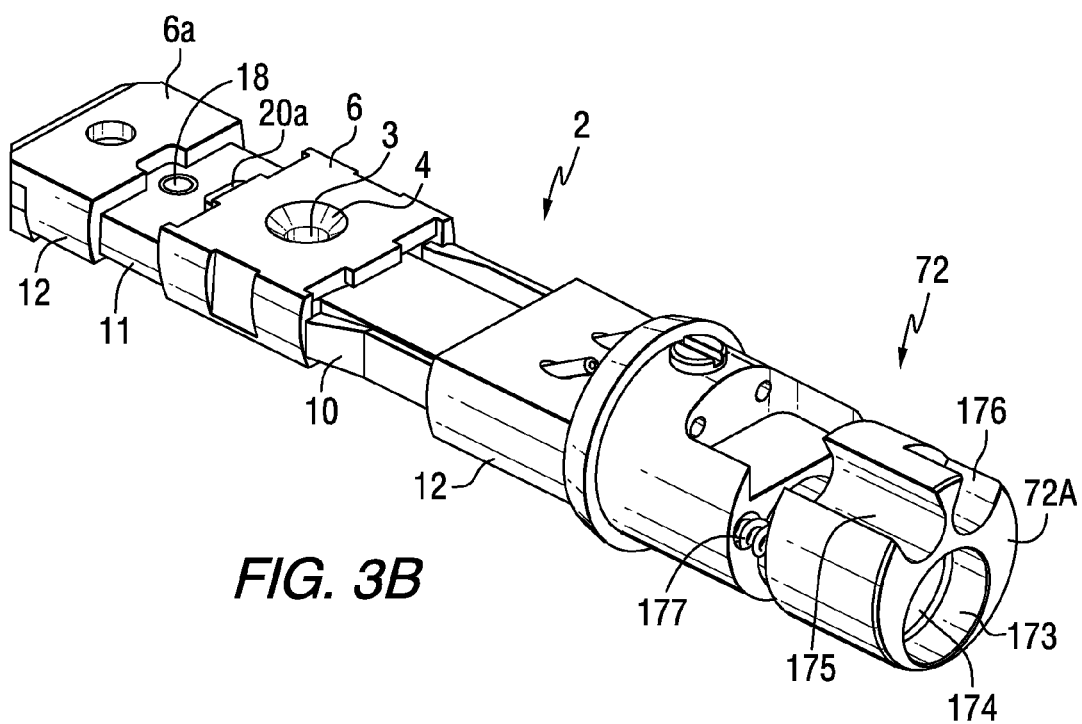
FIG. 3b is a bottom isometric view of the in situ holder tip assembly in accordance with an embodiment of the present invention.
Figure 3C:
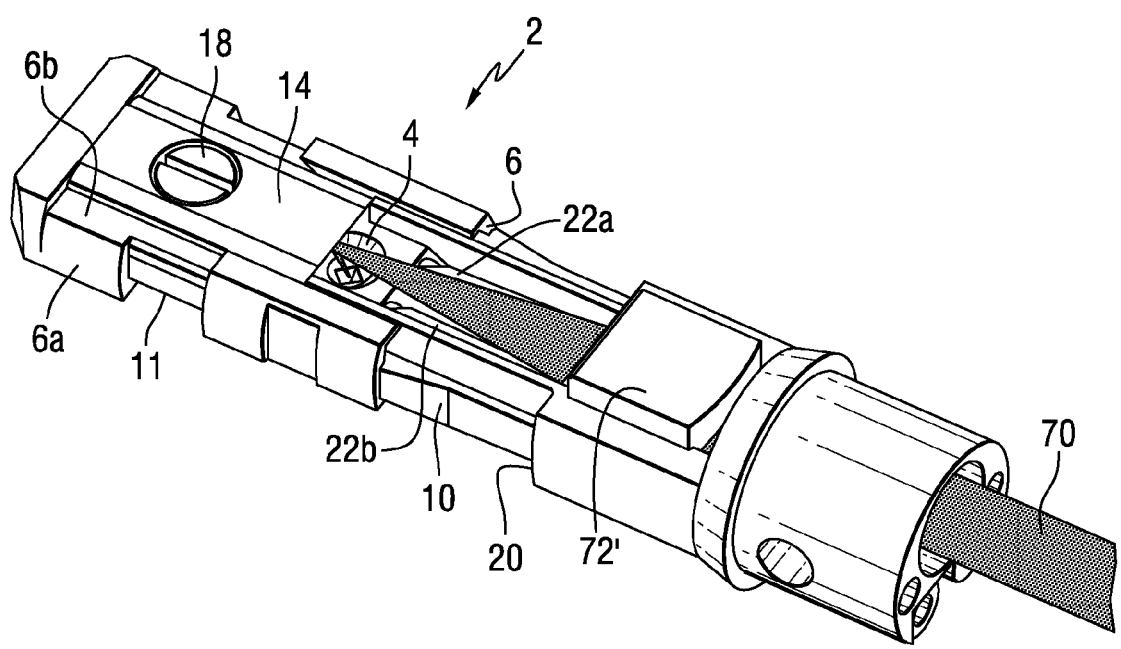
FIG. 3c is a bottom isometric view of the in situ holder tip assembly in accordance with a second embodiment of the present invention.
Figure 4:
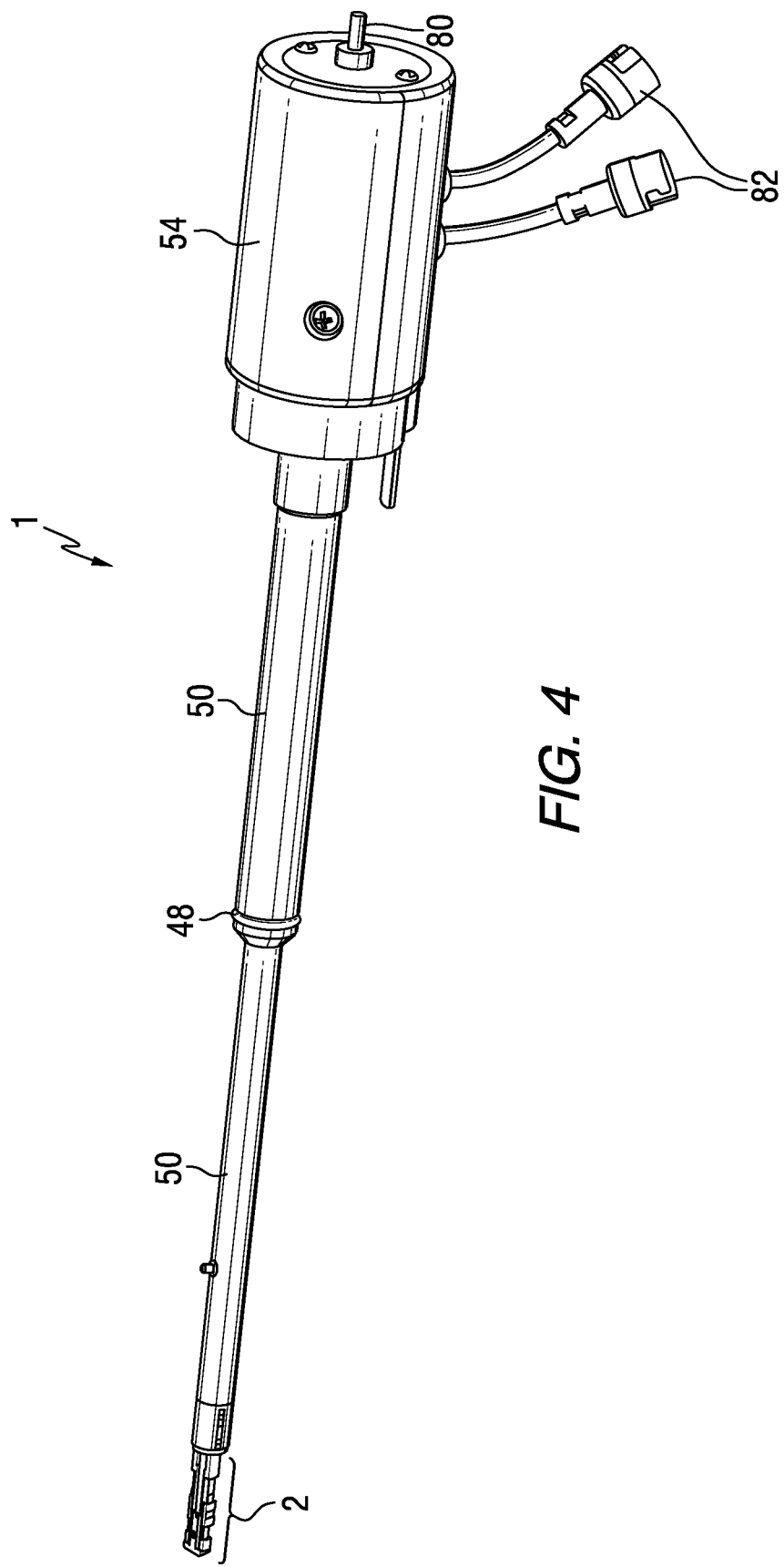
FIG. 4 is an isometric view of the specimen holder assembly.
Figure 4A:
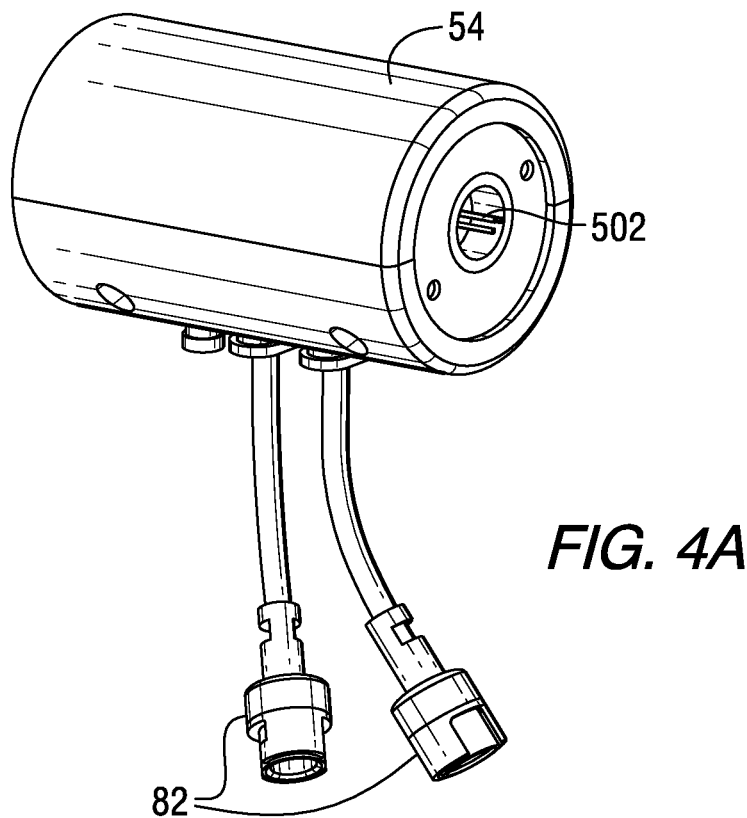
FIG. 4a is an isometric view of a second embodiment of the handle portion of the specimen holder assembly.
Figure 4B:
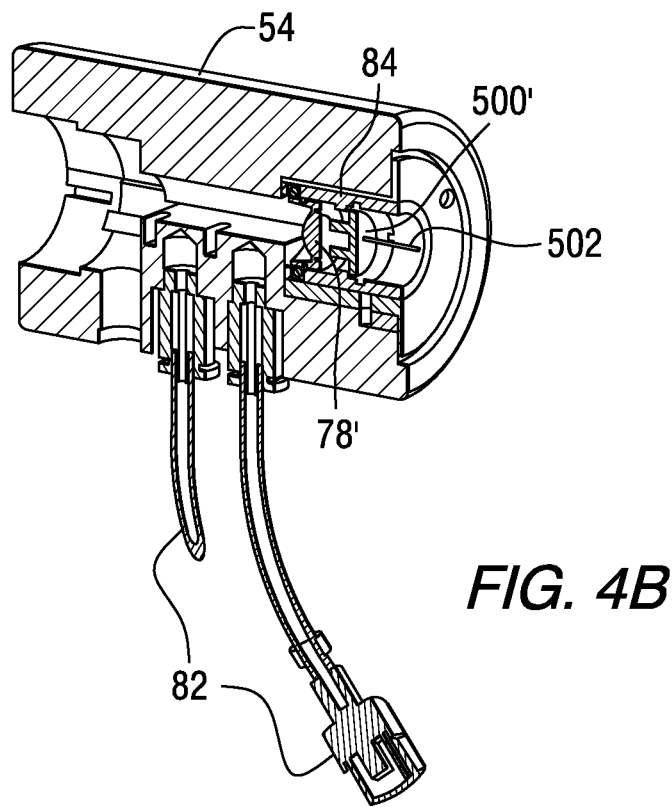
Figure 5:
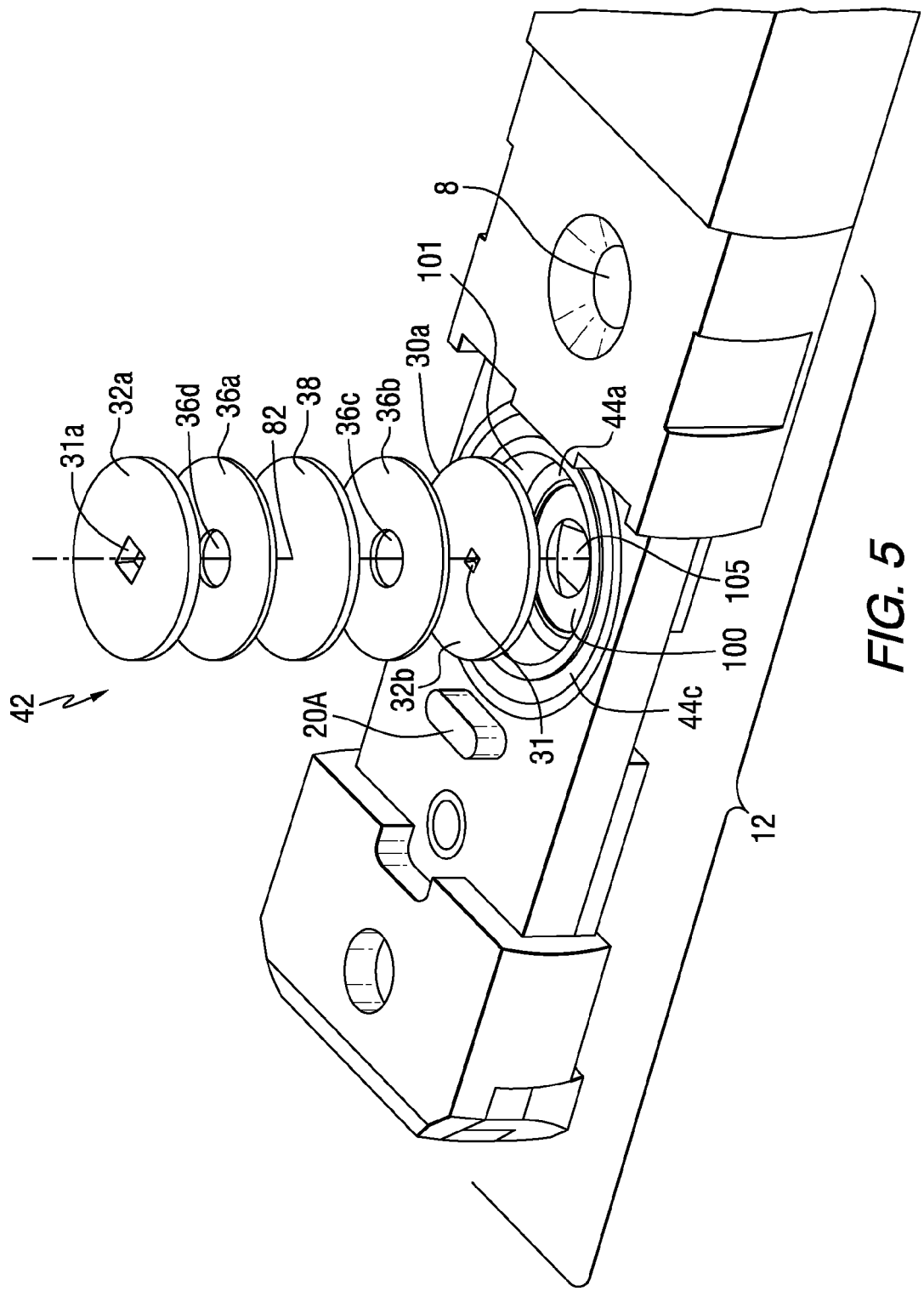
FIG. 5 is an exploded view illustrating the window and the spacer assembly within the environmental cell as viewed from the bottom.
Figure 8:
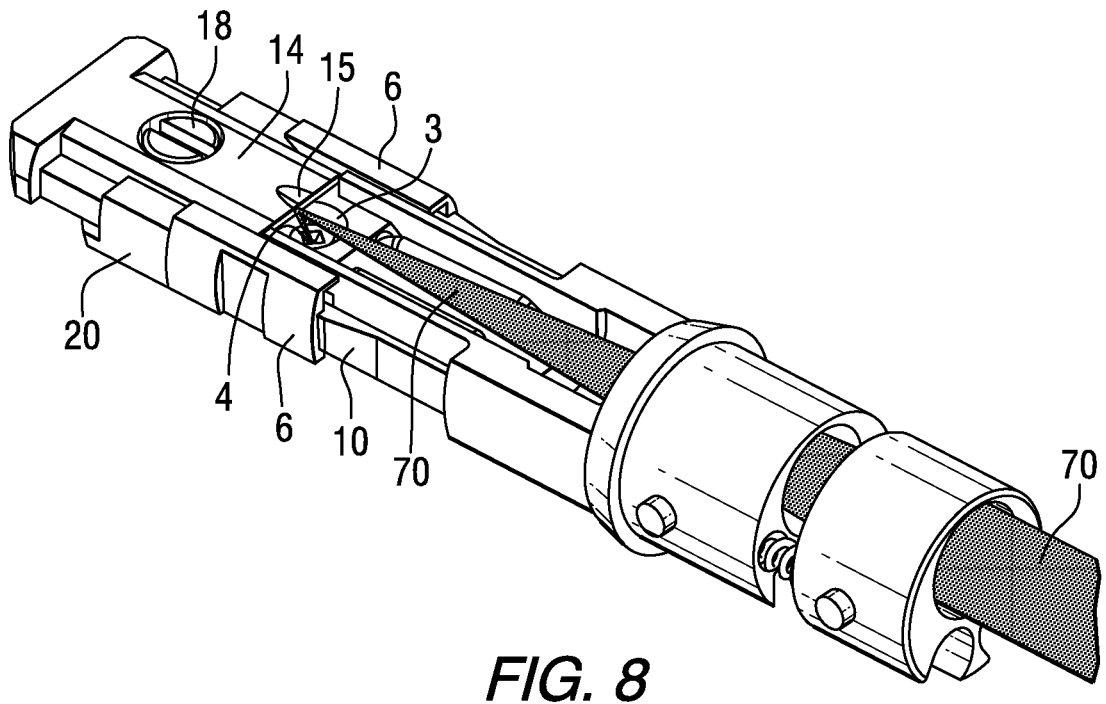
FIG. 8 is a diagrammatic isometric view of the holder tip illustrating the laser converging and reflection optics of the present invention.

Referring now to FIGS. 3a-3c, specimen holder tip 2 includes E-Cell 4. Lid 6 is slidably disposed on main body 12 of holder tip 2. Main body 12 is provided with a track 11 which is adapted to receive lid 6 and constrain its limited slidable displacement. Displacement of lid 6 provides access to E-Cell 4 on the underside of main body 12. A travel limiting stop 20 is provided at one end of main body 12 to restrict the travel of lid 6 in the open, or loading position, as shown in FIG. 5. Lid 6 may be slidably displaced from a position engaging stop 20 to a position engaging tangs 10 in the closed, or operative position, as illustrated in FIGS. 3a and 3b. Tangs 10 receive and restrain lid 6 in the operative position, as will be more fully described below. Travel of lid 6 in the closed position is further limited by travel stop 20A. E-Cell 4 is a cylindrical cavity, nominally 3.1 mm in diameter and 650 μm deep to accommodate a standard 3 mm diameter specimen disk.

E-cell assembly 42 is placed within the cavity while in the open position as more fully described with reference to FIG. 5. Once the E-Cell 4 is loaded, lid 6 is displaced to the operative position. Tangs 10 are resilient armatures having restraining profiles at the movable ends. Tangs 10 may therefore be displaced inwardly by applying manual pressure in a direction perpendicular to the longitudinal axis of main body 12. In order to relieve lid 6 from restraint by tangs 10 in the operative position, tangs 10 are depressed and lid 6 is slidably displaced (to the right in FIGS. 3a and 3b) to contact travel stop 20. In order to engage lid 6 with tangs 10 for restraint in the operative position, lid 6 is merely slidably displaced (to the left in FIGS. 3a and 3b) until tangs 10 engage a locking interface provided on lid 6 (not shown). A clamping mechanism for more securely engaging lid 6 to main body 12 when in the operative position is provided by clamp 6a which is slidably engaged with main body 12 along track 11, as will be more fully described below.

Main body 12 is provided with a series of recesses and conduits to accommodate fluid conduits 22 which will not be described further as being within the ambit of one skilled in the art. Fluid inlet and outlet conduits 22a and 22b, respectively, are a means for the environmental fluid to enter and exit E-cell 4. Although FIGS. 3a and 3b illustrate cylindrical fluid inlet and outlet conduits, one of skill in the art will recognize that other appropriately shaped conduits will serve the purpose of supplying fluid to the specimen. Appropriate fluid connections are provided throughout holder assembly 1 to fluidly communicate with connectors 82 in a conventional manner.

Mirror retainer assembly 14 is utilized to receive and support minor 15, which adapted to reflect the laser beam onto the specimen, as more fully discussed below. Minor 15 is bonded to minor retainer 14 at a precise, preselected angle or may be dynamically adjustable by external control. Minor retainer 14 is removably affixed to main body 12 by mounting screw 18.

Figure 9:
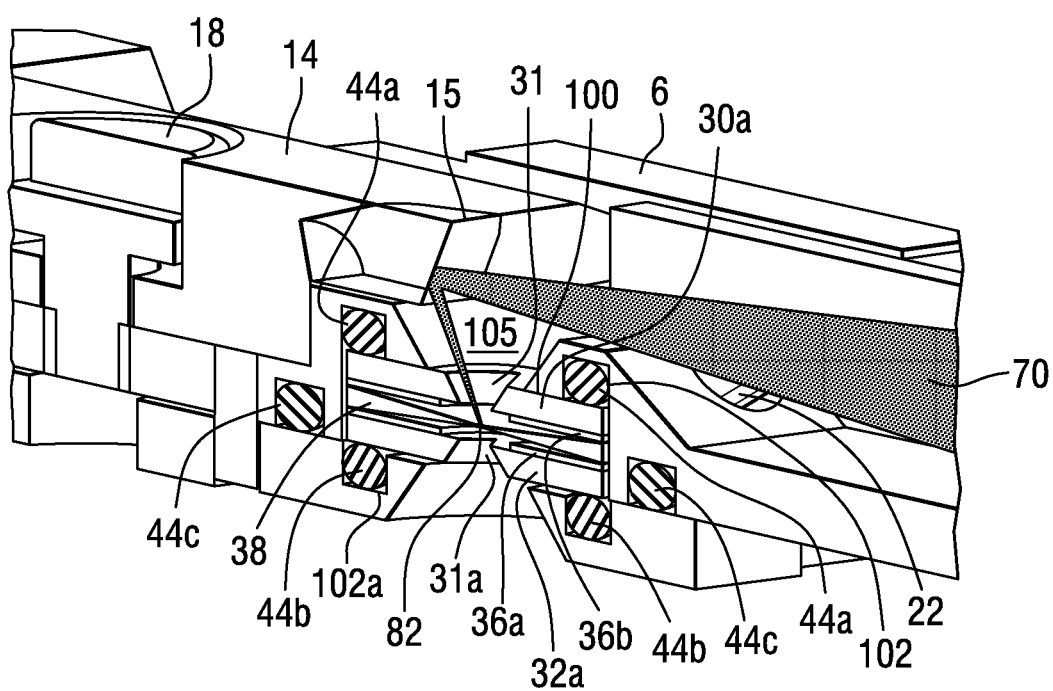
FIG. 9 is a diagrammatic sectional view of the environmental cell illustrating the laser beam striking the specimen.

Referring now to FIGS. 3, 5 and 9, E-Cell components 42 are assembled as a precisely sized unit having a particular height dimension to assist in maintaining a vacuum seal between lid 6 and main body 12. Main body 12 is provided with a mounting surface 100 disposed at the lower portion (as shown in FIG. 5) of E-Cell cavity 101. Mounting surface 100 is further provided with an O-ring receiving recess 102, as shown in FIG. 9, of conventional design. O-ring 44a is located within this recess 102. It is intended that the orifice within the E-Cell components 42 provides clear access for a laser beam to engage the specimen, as will be described more fully below. The first of the E-Cell assembly components, window frame 30a, constructed of silicon, is mounted within the E-Cell cavity 101 immediately adjacent mounting surface 100 and in sealing engagement with O-ring 44a. Window frame 30a is provided with a orifice 31 which is sized and shaped in any one of a variety of geometric shapes and is preferably square in two dimensions and frustopyramidal in three dimensions, with the larger end facing the incoming laser beam. An electron and electromagnetic radiation transparent membrane may be deposited on the orifice 31 and window frame 30a and presented as an integrated whole which is fluid impermeable. It is specifically noted that use of the membrane may be eliminated in certain applications to increase image resolution. Spacer 36b is mounted immediately adjacent window frame 30a and is disposed having an orifice 36c centrally located therein corresponding to orifice 31 of window frame 30a. Orifice 36c is generally larger in dimension than orifice 31. Specimen 38 is mounted immediately adjacent to spacer 36b and is typically a 3 mm diameter disk which has been appropriately thinned at the central point 82 for TEM imaging and analysis. Specimen 38 is optimally provided with an outer rim thickness of up to 200 µm. To obtain an electron transparent region, the specimen is thinned at the central region from a few nanometers to tens of nanometers. Other types of specimens can be particles dispersed onto a grid or FIB lamellae attached to a support structure. Spacer 36a and window frame 32a are provided with orifices 36d and 31a, respectively, and are mounted similarly to the corresponding spacer 36b and window frame 30a. The total assembly height is optimally 650 µm which corresponds to the E-cell cavity 101 depth. Spacers 36a and 36b act as thermal insulators and help obtain the desired fluid path length above and below the specimen, and further provide the interior space within the E-Cell 4 which contains the environmental fluid, as supplied to E-Cell cavity by fluid inlet conduit 22a and evacuated by fluid outlet conduit 22b in a conventional manner. E-cell cavity 101 is nominally designed to incorporate window frames having thicknesses ranging from about 75 µm to about 325 µm. The window membrane material must be electron transparent, able to withstand high temperature, pressure differentials in and around the chamber, and should not react with the fluid present within the chamber and may comprise, for example, silicon nitride, silicon oxide or amorphous silicon as dictated by user requirements. The thickness of window membranes 31, 31a is limited by the cell pressures desired within the E-Cell 4. In one preferred embodiment, window membranes 31 and 31a are constructed from silicon nitride deposited on a silicon substrate using low-pressure vapor deposition techniques (LPCVD). It has been shown that a pair of 15 nm thick silicon nitride membranes are able to withstand a pressure differential of up to one atmosphere. Diffused scattering of the electrons passing through the membrane increases with increasing thickness, degrading the attainable resolution. The thickness therefore should be minimized.

E-Cell assembly 4 is restrained within E-Cell cavity 101 by the action of lid 6. Lid 6 is provided with an O-ring receiving recess 102a, corresponding to recess 102 in main body 12, for receiving and restraining O-ring 44b. O-ring 44b provides a sealing engagement between lid 6 and window frame 32a. This sealing engagement, when lid 6 is in the operative position, causes E-Cell 4 to be restrained as a unit within E-Cell cavity 101 for imaging and analysis. Additional sealing of the E-Cell cavity is provided by O-ring 44c, disposed between main body 12 and lid 6. Additionally, clamp 6a is slidingly engaged with lid 6 to more securely depress lid 6 into engagement with E-Cell 4. Clamp 6a is provided with a wedge shaped armature 6b which is interposed between lid 6 and main body 12. Once lid 6 is engaged with tangs 10 in the operative position, clamp 6a is slidingly displaced along track 11 (as shown in FIG. 3a) such that armature 6b is increasingly interposed between lid 6 and main body 12 and its increasing height causes lid 6 to be pressed more completely against main body 12 on the side opposite armature 6b. This causes lid 6 to more fully compress O-rings 44a, b and c. It is to be specifically noted that those skilled in the art may utilize any sealing methodology other than O-rings to provide an enclosed environment for the E-Cell cavity 101 and other aspects of the holder assembly. This sealing mechanism provides the user with the flexibility of establishing a wide range of fluid lengths. The external height of the E-cell 4 is only 2.3 mm which is compatible with the objective pole pieces of most major commercially available TEMs.

In certain embodiments, the thickness of the components of the E-cell 4 may be adjusted to achieve a particular fluid path length above and below the specimen. However, the total height of the E-cell assembly 4 should not exceed 650 µm+/− 25 µm. Tables 1 and 2 illustrate two different configurations of the E-cell 4 components to achieve a path length of 250 µm and 10 µm respectively. This assembly is illustrated in FIGS. 6 and 7.

TABLE 1

Example of Variable E-cell Assembly Height

| | |
|---|---|
| Window Frame Thickness | 320 µm × 2 = 640 µm |
| Specimen Disk Thickness | 10 µm × 1 = 10 µm |
| TOTAL THICKNESS | 650 µm |
| FLUID PATH LENGTH CONFIGURATION | 10 µm |

TABLE 2

Example of Variable E-cell Assembly Height

| | |
|---|---|
| Window Frame Thickness | 200 µm × 2 = 400 µm |
| Specimen Disk Thickness | 200 µm × 1 = 200 µm |
| Top Spacer Thickness | 25 µm × 1 = 25 µm |
| Bottom Spacer Thickness | 25 µm × 1 = 25 µm |
| TOTAL THICKNESS | 650 µm |
| FLUID PATH LENGTH CONFIGURATION | 250 µm |

Table 1 shows an E-cell 4 configuration for use with thin specimens. In this embodiment, the spacers are not utilized in the assembly. The fluid path length totally comprises the specimen thickness of 10 µm. Table 2 shows an E-cell 4 configuration for use with thicker specimens. As illustrated, the fluid path length is 250 µm, corresponding to the combined height of the specimen 38 and the top and bottom spacers 36a and 36b. The major contributor to the relatively large fluid path length is the specimen 38 thickness. As illustrated in FIG. 6 the fluid path length configuration is 10 µm and in FIG. 7 the fluid path length configuration is 250 µm. The unique E-Cell 4 sealing mechanism provides the user with the flexibility to choose the desired fluid path length ranging from the specimen thickness to 500 µm. A fluid path length can be selected based on the required specimen temperature and the acceptable image resolution. If a very high specimen temperature is desired, it is recommended to have a greater fluid path length to minimize the negative effects of radiation.

The use of a laser in the present system allows for high precision, localized heating of the TEM specimen. The laser optical components for this holder are illustrated in FIGS. 3 and 8-10c. A standard laser connector 80, for example, in first, third and fourth embodiments, an SMA 905 laser connector, is provided at the handle 54 of the holder body (FIGS. 4 and 10a-c). Such laser connectors are well known in the art and therefore will not be explained in detail here. The desired laser 500 is connected to the holder using the SMA connector 80. The laser beam 70 then enters a collimator 78 in a first and third embodiment. Collimator 78 helps produce a parallel laser beam and prevents it from diverging as it travels along the length of the holder barrel towards the specimen tip 2. Collimator 78', in a second embodiment, operates in a like manner, but is mounted differently in conjunction with the internal laser 500'. The converging lens module 72 located at the holder tip 2 focuses the beam to a fine spot. Referring specifically to FIGS. 3a-c, converging lens module 72, 72' is illustrated, having a slidable lens body 72A in a first embodiment, and a unitary sliding lens 72' in a second, which are disposed within barrel 50 such that they may be displaced along the longitudinal axis of the holder assembly 1 or may be angularly displaced to permit translation of laser beam 70 across the face of specimen 38. An actuation rod (not shown) is inserted in port 176 and controls the longitudinal movement of lens body 72A or lens 72'. This movement changes the focus and/or position of the laser beam and therefore the beam diameter at the point of contact with specimen 38. A fluid line conduit 175 is located within lens body 72A to permit the displacement of lens body 72A without interference with the passage of the environmental fluid into E-Cell 4. Lens 174 is partially visible in FIG. 3b and comprises at least one movable element which is utilized to focus the laser beam. Lens body 72A is laterally displaced with respect to main body 12 and is resiliently affixed thereto by springs 177. The small diameter laser beam 70 strikes the laser mirror 15 and is reflected to a precise location on the specimen 38 within E-cell 4. Depending on the wavelength of the electromagnetic radiation and the focal length of the converging lens, the focused beam spot size at the specimen can be varied from a few to hundreds of microns. The collimator 78, 78', converging lens module 72, 72' and the mirror 15 are precisely aligned so that the laser beam 70 clears the window frame 30a through orifice 31 and strikes the specimen in the vicinity of the center point 82. The window membrane is transparent to the laser beam 70 and does not absorb or reflect it. As a result, a radial symmetric heating zone is generated on the specimen. This allows for uniform expansion of the specimen at high temperatures, thus minimizing specimen drift.

Figure 10A:
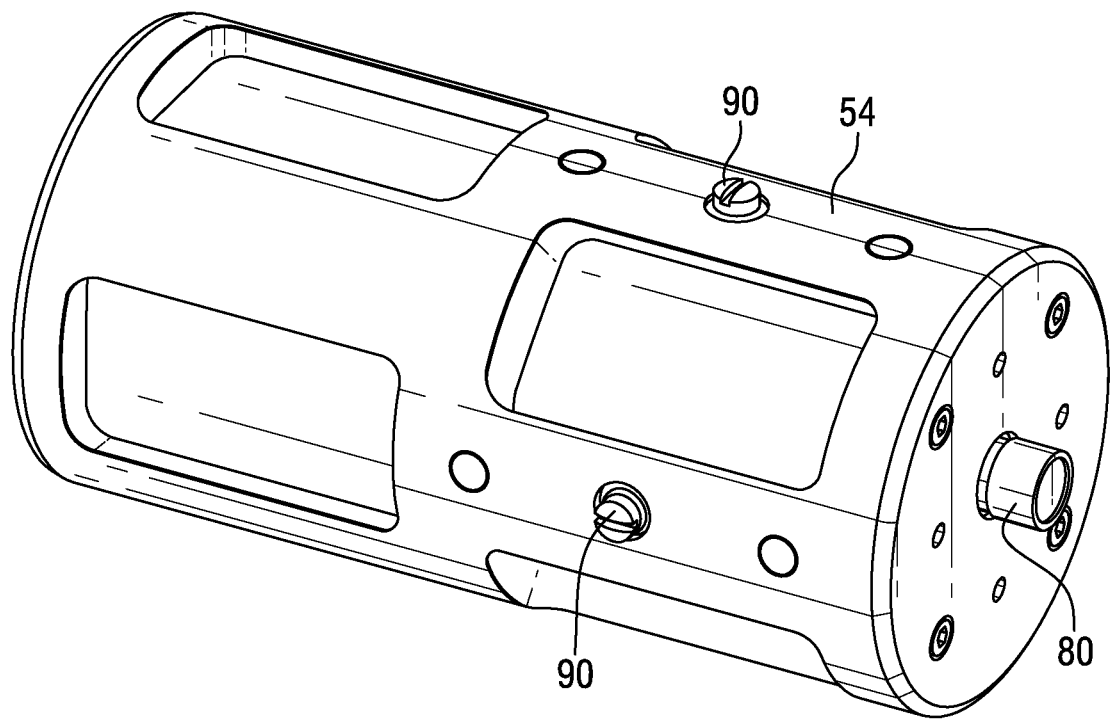
FIG. 10a is an isometric view of a third embodiment of the handle portion of the specimen holder assembly.
Figure 10B:
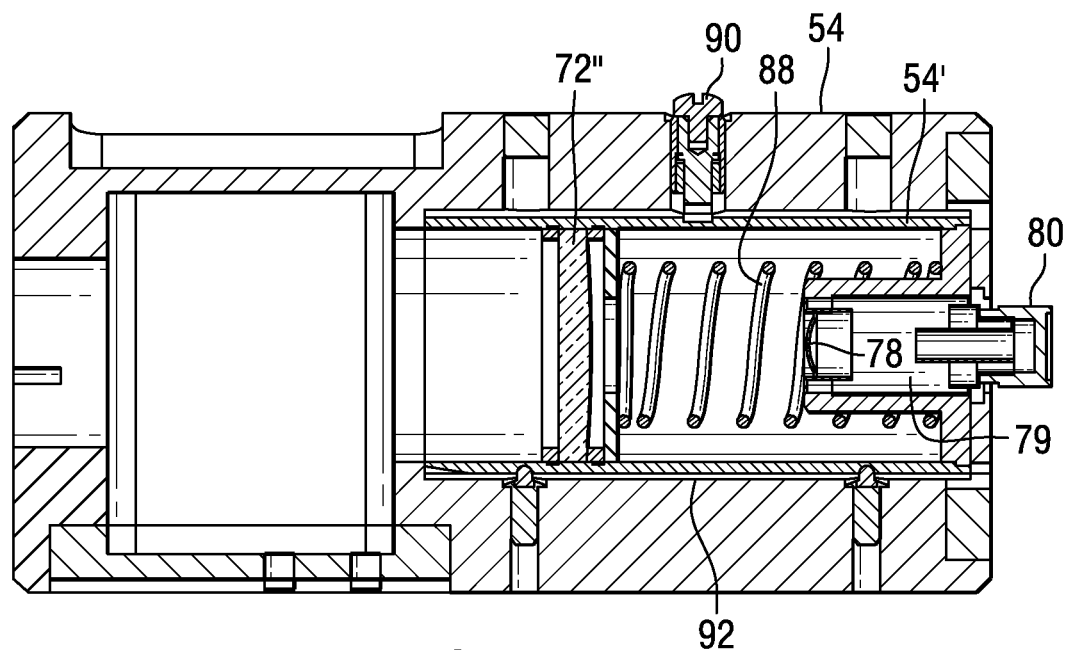
Figure 10C:
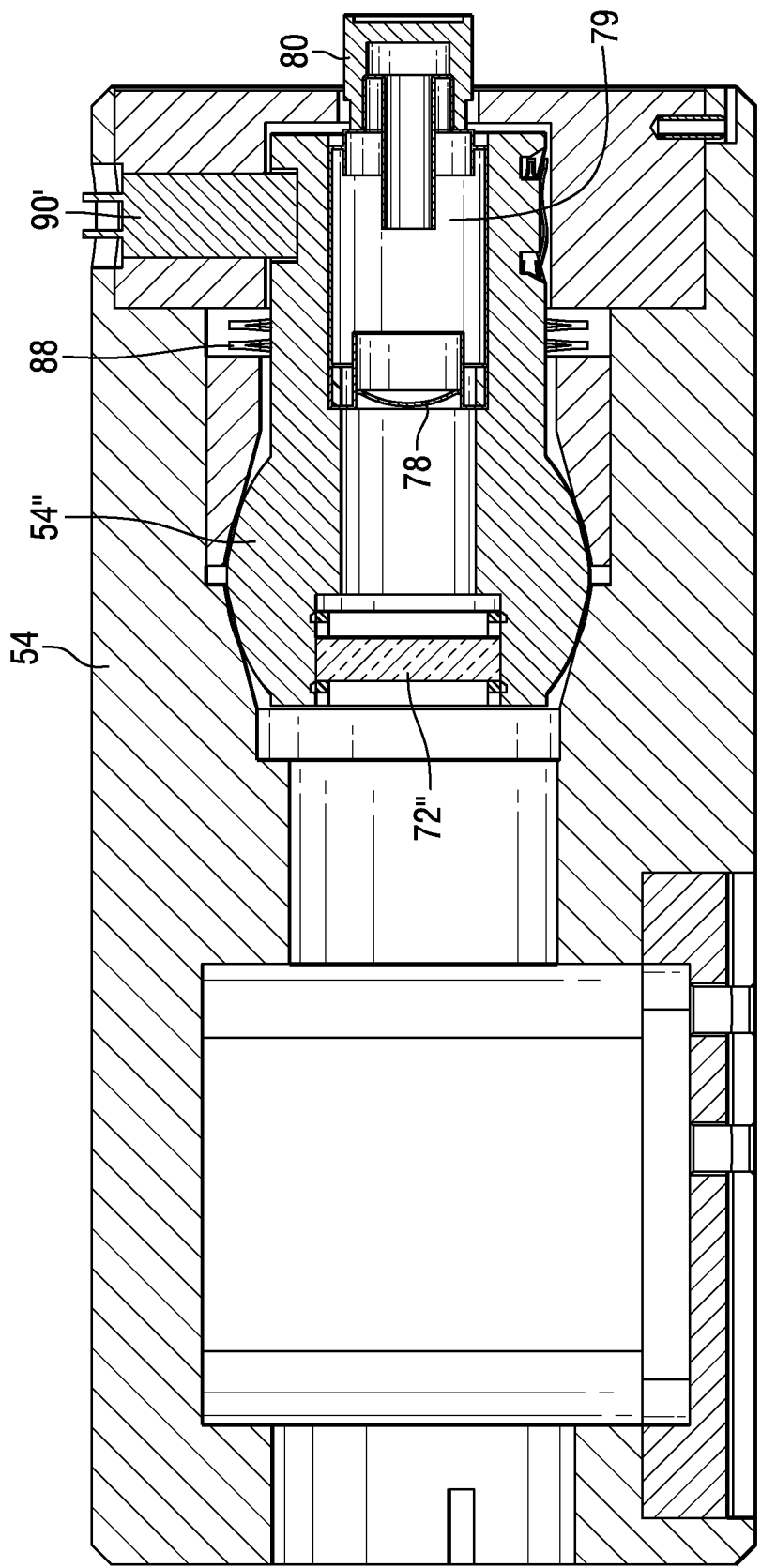
FIG. 10c is a sectional view of a fourth embodiment of the handle portion of the specimen holder assembly.

Alternative third and fourth embodiments of the handle 54 are illustrated in FIGS. 10a-10c. The interface with the laser source 500 is similar to the first embodiment, having an SMA connector 80. The laser beam is introduced into an optical assembly 54', 54", at the end of which collimator lens 78 is located. A converging lens 72" is located within an optical assembly 54', 54" which is removable from and engaged with handle 54. Converging lens 72" is axially adjustable within optical assembly 54', 54" by manual, as illustrated in FIG. 10a-b, or electromechanical, as illustrated in FIG. 10c, displacement within its bore. A resilient spring member 88 biases converging lens 72" in a direction away from the laser source. Such movement of the converging lens 72" modifies the beam diameter of laser beam 70. The optical assembly 54', 54" is also axially and rotationally adjustable within handle 54, permitting displacement of laser beam 70 along the surface of the specimen 38. In the third embodiment, illustrated in FIGS. 10a-b, adjustment screws 90 are provided in the X and Y axes at 90° angles with respect to each other. Each provides a micrometer-type mechanical adjustment and displacement of the optical assembly 54' within the bore 92 of the housing. Support, sealing and lubrication of all components are consistent with like parts as described herein and within the ambit of one skilled in the art to modify for the particular component geometry encountered. In the fourth embodiment, illustrated in FIG. 10c, a piezo actuator 90' is utilized to adjust the orientation of the optical assembly 54". The electromechanical properties and application of the piezo actuator are well within the ambit of one skilled in the art.

The laser optics of the present invention, i.e., collimator 78, 78', converging lens 72, 72' and mirror 15, act together to precisely focus laser beam 70 onto the E-cell 4 to attain high specimen temperatures. The maximum temperature that can be attained on the specimen is limited largely by the material properties of the specimen and the laser 500, 500' power, thus creating a potential for applications in an extraordinary range of fields. The inventors have found that less than 1 Watt of laser energy was required to raise the specimen temperature to 2,000° C. An additional advantage of the presently described specimen laser spot heating is the speed in which the steady state specimen temperature is achieved. Most specimen reactions occur instantly once a critical temperature is obtained. Standard TEM heating holders utilizing resistive heaters have a slow heating response time and it takes a considerable amount of time to reach a steady state specimen temperature. The laser optics utilized in the present holder achieves sub millisecond heating response times due to the small heating zone. As a result, steady state specimen temperature is achieved instantly. The laser beam 70 can easily be modulated to provide dynamic thermal cycling of the specimen between ambient and elevated temperatures. Pulsed lasers can be attached to the holder to provide pulses of energy within a time frame as small as few nano seconds.

In addition, the laser heating system of the present invention is adjustable so that it may be used with a wide variety of specimens. The spot size of laser beam 70 may be adjusted by longitudinal displacement of lens body 72, 72'. This allows the flexibility of changing the laser power density. For example, it is possible to first melt a 10 μm hole in the specimen at high laser power density, thus locating the laser beam position within the microscope. The laser beam 70 may then be relocated to any relative point on the surface of the specimen through the displacement of mirror 15 and/or optical assembly 54'. The laser beam size may also be varied to obtain the desired specimen temperature in the vicinity of the hole.

Figure 11:
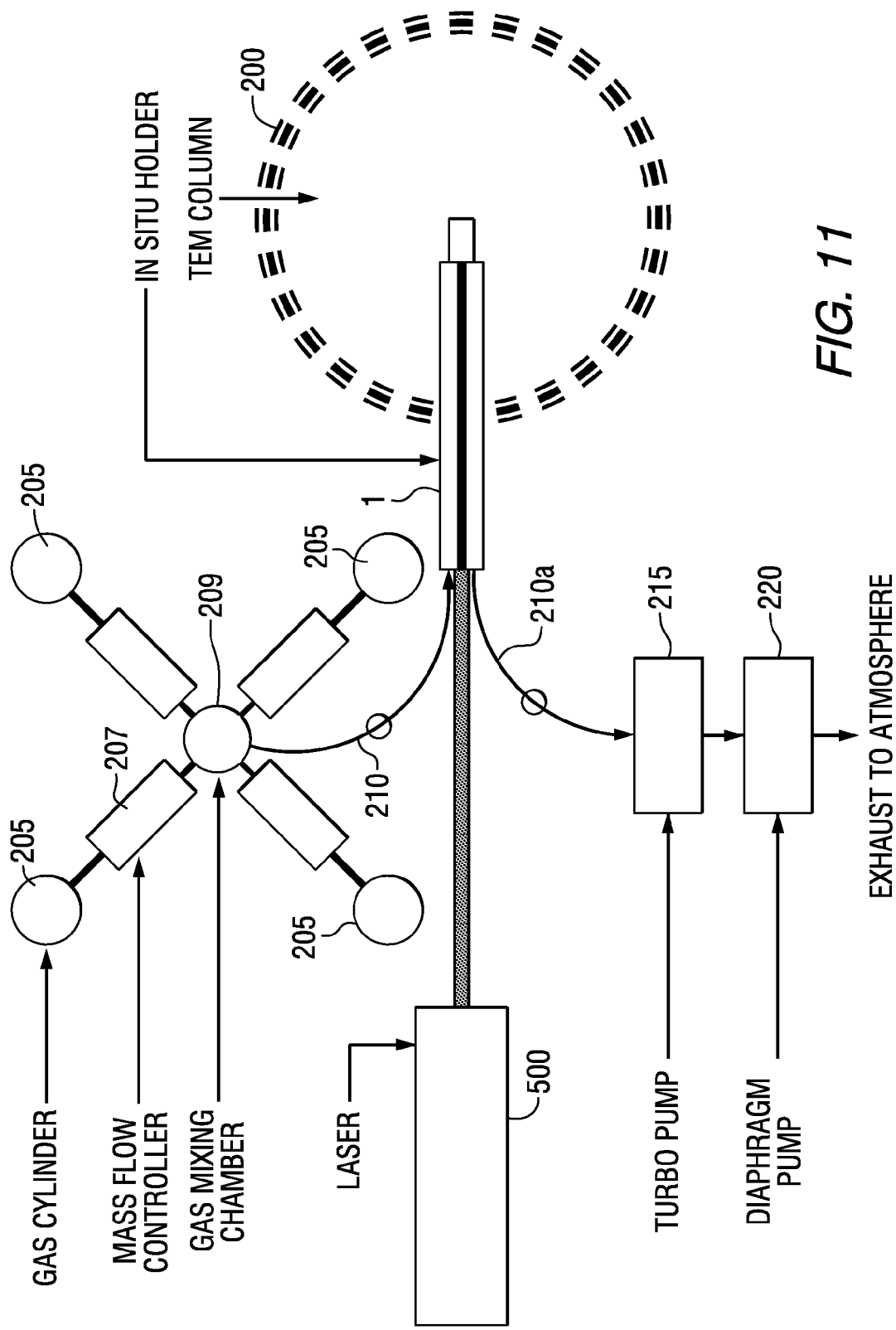
FIG. 11 is a diagrammatic functional illustration of the in situ holder integrated with a gas delivery and imaging system of a transmission electron microscope.

Referring now to FIG. 11, the fluid flow assembly design has the provision of flowing up to four different gases simultaneously through the cell. The various gases are provided in conventional cylinders 205 which are each in fluid communication with mass flow controllers 207. Mass flow controllers regulate the flow of gas under either manual or computer-operated control. A gas mixing chamber 209 is provided which combines the selected gases into a uniform composite which may be flowed to the holder assembly 1 through supply line 210. Supply line 210 is affixed to the appropriate fluid connector 82 and subsequently to fluid supply conduit 22a. The uniform gas mixture is then circulated into the E-Cell 4. The continuous flow of gas is maintained with the help of the pressure differential generated between the inlet and the outlet ports of the holder by turbo molecular pump 215 mounted externally and the internal pressure of gas cylinder 205. This pump in combination with diaphragm pump 220 and mass flow controllers 207 continuously flow the gas or gas mixture to supply the appropriate pressure within E-Cell 4, by means of gas exhaust line 210a and gas supply line 210. The primary consideration given towards the design of the gas flow system is the attainable pressure within E-cell 4. Higher gas pressures can be achieved by switching off the differential pumps and maintaining a steady flow of gas into E-Cell 4. The pressure inside E-Cell 4 may be varied by simultaneously pumping the cell and/or regulating the mass flow rate of the gases. Gas flow regulation as well as adjustments to the laser power may be either manually or computer controlled utilizing a standard computerized interface such as Labview, a program developed by National Instruments.

Similarly, an external liquid circulation unit can be attached to the holder in a similar fashion to incorporate biological applications that require the flow of liquids through the cell.

The terms and expressions which have been employed herein are used as terms of description and not as limitation, and there is no intention in the use of such terms and expressions of excluding equivalents of the features shown and described or portions thereof, it being recognized that various modifications are possible within the scope of the invention claimed. Although particular embodiments of the present invention have been illustrated in the foregoing detailed description, it is to be further understood that the present invention is not to be limited to just the embodiments disclosed, but that they are capable of numerous rearrangements, modifications and substitutions.

What is claimed is:

1. A specimen holder which receives and positions a specimen in an imaging device, said holder comprising:
   a receptacle for receiving and supporting said specimen;
   an elongated barrel mounted between said receiver and said receptacle for positioning said specimen at a preselected location within said imaging device and for containing said beam of electromagnetic radiation;
   a self-contained electromagnetic radiation source and
   an adjustable lens;
   said self-contained electromagnetic radiation source and said adjustable lens mounted within said elongated barrel for receiving and focusing said beam of electromagnetic radiations on said specimen at a focus point, said beam of electromagnetic radiations causing an increase in the energy level of a portion of said specimen proximate to the focus point of said beam of optical energy.

2. A specimen holder as described in claim 1, wherein said beam of electromagnetic radiation is selected from the group consisting of an electron beam, infrared radiation, visible light, ultraviolet radiation and X rays.

3. A specimen holder as described in claim 1, wherein said beam of electromagnetic radiation has a wavelength between 0.01 nm to 300 µm.

4. A specimen holder as described in claim 3, wherein said beam of electromagnetic radiation has a wavelength between 1 µm to 1.1 µm.

5. A specimen holder as described in claim 1, further comprising means for collimating said beam of electromagnetic radiation.

6. A specimen holder as described in claim 5, wherein said collimating means is axially adjustable.

7. A specimen holder as described in claim 1, wherein said adjustable lens further comprises a converging lens which focuses said beam of electromagnetic radiations into a focus point having a variable spot size.

8. A specimen holder as described in claim 7, wherein said beam of electromagnetic radiation is an infrared laser and said variable spot size is adjusted by said adjustable lens between 10 µm to 500 µm.

9. A specimen holder as described in claim 8, wherein said beam of electromagnetic radiation is an infrared laser and said variable spot size is adjusted by said adjustable lens between 10 µm to 60 µm.

10. A specimen holder as described in claim 7, wherein said variable spot size is adjusted by said adjustable lens between 10 µm to 3 mm.

11. A specimen holder as described in claim 1, wherein said focus point is translated across said specimen by said adjustable lens.

12. A specimen holder as described in claim 5, wherein said focus point is translated across said specimen by at least one of said adjustable lens and said collimating means.

13. A specimen holder as described in claim 5, wherein said collimating means further comprises a converging lens.

14. A specimen holder as described in claim 5, wherein said focus point is translated across said specimen by at least one of mechanical and electromechanical control.

15. A specimen holder as described in claim 5, wherein said mechanical control further comprises a micrometer adjuster.

16. A specimen holder as described in claim 5, wherein said electromechanical control further comprises a piezoelectric actuator.

17. A specimen holder as described in claim 1, wherein said focus point is a well defined beam spot on the specimen having even and symmetric concentric thermal energy distribution across the diameter of the specimen.

18. A specimen holder as described in claim 1, wherein said adjustable lens further comprises a polished surface to focus said beam of electromagnetic radiation into said focus point.

19. A specimen holder as described in claim 18, wherein said polished surface further comprises a mirror.

20. A specimen holder as described in claim 18, wherein said mirror is adjustable.

21. A specimen holder as described in claim 18, wherein said mirror is selected from the group consisting of convex, concave and spherical.

22. A specimen holder as described in claim 1, further comprising:
   a closed cell receptacle for receiving and supporting said specimen, said closed cell receptacle having an internal chamber for containing a controlled environment therein, said closed cell receptacle being transparent with respect to said imaging device;
   at least one port for introduction of fluid components of said controlled environment; and
   an elongated barrel mounted between said receiver and said receptacle for positioning said specimen at a preselected location within said imaging device and having at least one conduit for transmitting said fluid components of said controlled environment from said port to said internal chamber.

23. A specimen holder as described in claim 22, wherein said receptacle further comprises a main body having said internal chamber therein.

24. A specimen holder as described in claim 22, wherein said internal chamber is sealed by a lid assembly.

25. A specimen holder as described in claim 22, wherein said lid assembly is displaceable with respect to with said main body.

26. A specimen holder as described in claim 25, wherein said lid assembly further comprises an orifice which is transparent to said imaging device.

27. A specimen holder as described in claim 25, wherein said lid assembly may be fixed in an operative position.

28. A specimen holder as described in claim 22, wherein said internal chamber further comprises an orifice which is transparent to said imaging device.

29. A specimen holder as described in claim 22, wherein said orifice of said internal chamber is aligned with said orifice of said lid assembly when said lid assembly is in an operative position and sealing said internal chamber.

30. A specimen holder as described in claim 22, wherein said internal chamber further comprises at least one sealing window which is transparent to said imaging device which is mounted adjacent at least one of said orifice of said internal chamber and said orifice of said lid assembly.

31. A specimen holder as described in claim 30, wherein said specimen is mounted adjacent said at least one sealing window.

32. A specimen holder as described in claim 30, further comprising at least one spacer mounted between said specimen and said at least one sealing window.

33. A specimen holder as described in claim 32, wherein said spacer further comprises an orifice which is transparent to said imaging device.

34. A specimen holder as described in claim 32, wherein said specimen is interposed between a plurality of spacers and a plurality of sealing windows to form an environmental cell mounted within said internal chamber.

35. A specimen holder as described in claim 32, wherein said at least one spacer and said specimen form a secondary chamber which contains said controlled environment.

36. A specimen holder as described in claim 30, wherein said at least one sealing window has an interior surface.

37. A specimen holder as described in claim 36, wherein a plurality of sealing windows are mounted within said internal chamber such that said interior surfaces are facing each other.

38. A specimen holder as described in claim 37, wherein the distance between said plurality of sealing window interior surfaces is adjustable between 0 and 500 microns.

39. A specimen holder as described in claim 22, further comprising an external fluid delivery system for introduction of said fluid to generate said controlled environment.

40. A specimen holder as described in claim 22, wherein said fluid further comprises at least one process gas or liquid.

41. A specimen holder as described in claim 22, wherein said fluid further comprises a plurality of process gases or liquids which are combined prior to introduction to the internal chamber.

* * * * *